(12) United States Patent
Tang et al.

(10) Patent No.: US 8,592,539 B2
(45) Date of Patent: Nov. 26, 2013

(54) PREPARATION OF COBALTOCENIUM-CONTAINING MONOMERS AND THEIR POLYMERS

(75) Inventors: Chuanbing Tang, Columbia, SC (US); Lixia Ren, Columbia, SC (US)

(73) Assignee: University of South Carolina, Columbia, SC (US)

( * ) Notice: Subject to any disclaimer, the term of this patent is extended or adjusted under 35 U.S.C. 154(b) by 239 days.

(21) Appl. No.: 13/209,759

(22) Filed: Aug. 15, 2011

(65) Prior Publication Data

US 2012/0041163 A1    Feb. 16, 2012

Related U.S. Application Data

(60) Provisional application No. 61/401,602, filed on Aug. 16, 2010.

(51) Int. Cl.

| C08F 30/04 | (2006.01) |
|---|---|
| C07F 17/02 | (2006.01) |
| C08F 297/00 | (2006.01) |
| B01J 41/08 | (2006.01) |
| H01M 4/60 | (2006.01) |

(52) U.S. Cl.
USPC ............ 526/241; 526/923; 521/38; 525/274; 528/9; 528/354; 556/143; 556/145

(58) Field of Classification Search
USPC ............... 526/241, 923; 525/274; 528/354, 9; 521/38; 556/143, 145
See application file for complete search history.

(56) References Cited

FOREIGN PATENT DOCUMENTS

SU    1145023    *  3/1985

OTHER PUBLICATIONS

Caplus Abs. AN 1985:406896 of SU 1145023 (Mar. 1985).*
Ren, et al, "Synthesis and Solution Self-Assembly of Side-Chain Cobaltocenium-Containing Block Copolymers," J. Am. Chem. Soc. 2010, 132, 8874-8875 (Pub. Date (Web): Jun. 14, 2010).*
Schottenberger, et al, "Mixed-membered-bisfulvalene dimetal-complexes via metallocene-substituted norbornenyl alcohols," J. Organometallic Chem. 541 (1997) 249-260.*
Wang, et al, "Controlled/Living Radical Polymerization of MMA Catalyzed by Cobaltocene," Macromolecules 2003, 36, 9684-9686.*
Meneghetti, et al, "Reactivity of Cyclocobaltated Benzylamine Derivatives toward Terminal Alkynes," Organometallics 2000, 19, 1935-1939.*
Mayer, et al, "Ring-Opening Polymerization of 19-Electron [2]Cobaltocenophanes . . . ," J. Am. Chem. Soc. 2009, 131, 10382-10383.*
Cuadrado, et al, "Preparation and Redox Properties of Novel Polymerizable Pyrrole- and Allyl-Functionalized Cobaltocenium Monomers and Siloxane-Based Cobaltocenium Polymers," Organometallics 1999, 18, 4960-4969.*

(Continued)

Primary Examiner — Fred M Teskin
(74) Attorney, Agent, or Firm — Dority & Manning, P.A.

(57) ABSTRACT

Methods of forming a cobaltocenium-containing polymer are provided through polymerizing a plurality of cobaltocenium-containing monomers via controlled radical polymerization or controlled ring-opening polymerization. Each cobaltocenium-containing monomer comprises a cobaltocenium moiety covalently connected to a polymerizable group. Cobaltocenium-containing monomers are also provided that include a cobaltocenium moiety covalently connected to a polymerizable group. Cobaltocenium-containing polymers are also generally provided, such as the polymers formed according to any of the methods or from any of the monomers discussed herein. Methods are also generally provided for exchanging an anion associated with a cobaltocenium side group of a cobaltocenium-containing polymer with a new anion.

23 Claims, 14 Drawing Sheets

(56) References Cited

OTHER PUBLICATIONS

Ito, et al, "Ion-exchange Properties of Anion-Exchanger Containing Cobalticinium Cations," Bulletin of Chem. Soc. of Japan, vol. 41 (1968) No. 7, 1600-1605.*

Nguyen et al., "Organometallic Polymers with Transition Metals in the Main Chain". Chem. Rev. 1999, 99, 1514-1548.

Korczagin et al., "Surface Nano- and Microstructuring with Organometallic Polymers". Adv Polym Sci, 2006, 200, 91-117.

Hudson, "Ferrocene polymers: current architectures, syntheses and utility". Journal of Organometallic Chemistry 637-639, 2001, 47-69.

Bunz, "Carbon-Rich Molecular Objects from Multiply Ethynylated-Complexes". Topics in Current Chemistry, 1999, 201, 131-161.

Sheats et al., "Synthesis and Properties of Cobalticinium Salts. I. Synthesis of Monosubstituted Cobalticinium Salts". J . Org. Chem., 1970, 36, 10, 3245-3249.

Astruc et al., "Metallocenyl Dendrimers and Their Applications in Molecular Electronics, Sensing, and Catalysis". Accounts of Chemical Research, 2008, 41, 7, 841-856.

Mayer et al., "Ring-Opening Polymerization of 19-Electron [2]Cobaltocenophanes: A Route to High-Molecular-Weight, Water-Soluble Polycobaltocenium Polyelectrolytes". J. Am. Chem. Soc., 2009, 131, 30, 10382-10383.

Carraher et al., "Synthesis of organometallic polymers by the interfacial technique". Die Makromolekulare Chemie, 1973, 166, 1, 23-29.

Pittman et al., "Organometallic polymers, Condensation polymerization of cobalticinium salts". Die Makromolekulare Chemie, 1974, 175, 5, 1427-1437.

Cuadrado et al., "Preparation and Redox Properties of Novel Polymerizable Pyrrole- and Allyl-Functionalized Cobaltocenium Monomers and Siloxane-Based Cobaltocenium Polymers". Organometallics, 1999, 18, 4960-4969.

Ren et al., "Synthesis and Solution Self-Assembly of Side-Chain Cobaltocenium-Containing Block Copolymers". J. Am. Chem. Soc., 2010, 132, 8874-8875.

* cited by examiner

PREPARATION OF COBALTOCENIUM-CONTAINING MONOMERS AND THEIR POLYMERS

PRIORITY INFORMATION

The present application claims priority to U.S. Provisional Patent Application Ser. No. 61/401,602 filed Aug. 16, 2010 of Tang, et al. titled "Preparation of Cobaltocenium-containing Vinyl Monomers and Their Polymers", the disclosure of which is incorporated by reference herein.

BACKGROUND

Metallocene-containing polymers have been widely utilized for applications ranging from electrochemical sensors to templates for advanced materials to biomedicines, due to their unique physicochemical properties. Cobaltocenium, an 18-e analogue to extensively studied ferrocene, is a cationic metallocene, which possess superior chemical stability, high redox potential and counter-ion dependent solubility. Thus the integration of cobaltocenium into polymeric materials has great potential applications as cationic polyelectrolytes.

Among the metallocene polymers, ferrocene-containing polymers are the mostly studied. Different from ferrocene (18e), cobaltocene (19e) has one more electron, and it can lose one electron readily to form stable cobaltocenium (18e), isoelectronic with ferrocene. Cobaltocenium polymers are much less explored than ferrocene polymers due to the difficulty in synthesis of cobaltocenium derivatives. Different from ferrocene polymers, cobaltocenium polymers are polyelectrolytes with solubility in polar solvents such as water and dimethylformamide.

However, the preparation of side-chain cobaltocenium-containing polymers is challenging due to the lack of efficient controlled polymerization and facile macromolecular engineering, although a few main-chain cobaltocenium polymers have been synthesized via condensation or ring-opening polymerization. As such, a need exists for methods for the synthesis of cobaltocenium-containing monomers and their corresponding side-chain cobaltocenium-containing polymers.

SUMMARY

Objects and advantages of the invention will be set forth in part in the following description, or may be obvious from the description, or may be learned through practice of the invention.

Methods are generally provided of forming a cobaltocenium-containing polymer through, for example, polymerizing a plurality of cobaltocenium-containing monomers via controlled radical polymerization or controlled ring-opening polymerization. Each cobaltocenium-containing monomer comprises a cobaltocenium moiety covalently connected to a polymerizable group. Particularly suitable polymerizations can include, but are not limited to, reversible addition-fragmentation chain transfer polymerization (e.g., where the polymerizable group comprises a vinyl group, such as an acrylate moiety, a methacrylate moiety, a styrene moiety, an acrylamide moiety, etc.). In one embodiment, the polymerizable group can include a norbornene moiety, which can be particularly suitable for polymerization via ROMP. In another embodiment, the polymerizable group can include a strained ester ring, which can be particularly suitable for polymerization via ROP.

The cobaltocenium-containing polymer formed can be a homopolymer or a copolymer (e.g., a block copolymer). In one particular embodiment, the cobaltocenium-containing monomer can be polymerized with a second plurality of second monomers (e.g., where the second monomers are non-cobaltocenium-containing monomers).

The cobaltocenium moiety can be covalently connected to a polymerizable group directly, or can be covalently connected to the polymerizable group indirectly through a linkage between the cobaltocenium moiety and the polymerizable group. The linkage can include, for example, an alkyl group, an alkene group, an ester group, etc., or a combination thereof.

Cobaltocenium-containing monomers are generally provided that include a cobaltocenium moiety covalently connected to a polymerizable group, wherein the polymerizable group is configured to be polymerized via controlled living polymerization or controlled ring-opening polymerization.

Cobaltocenium-containing polymers are also generally provided, such as the polymers formed according to any of the methods or from any of the monomers discussed herein.

Methods are also generally provided for exchanging an anion associated with a cobaltocenium side group of a cobaltocenium-containing polymer with a new anion. The new anion can be, for example, a hydroxyl ion, a halide ion, a nitrate ion, a hexafluorophosphate ion, a tetraphenylborate ion, or mixtures thereof.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

DETAILED DESCRIPTION

Figure 1:
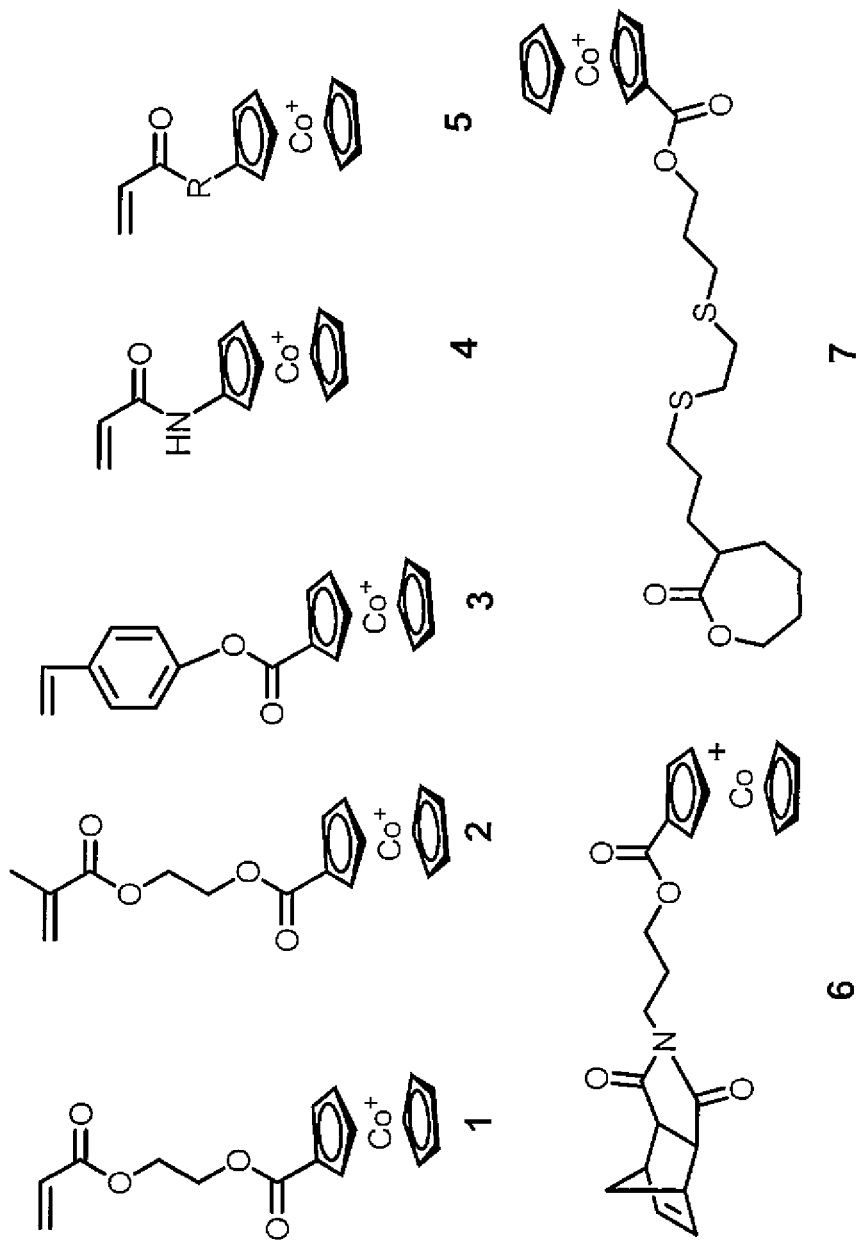
FIG. 1 shows an example of acrylate, methacrylate, styrene, acrylamide-type, norbornene, and a strained ester ring of cobaltocenium vinyl monomers.

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, the present disclosure is directed to side-chain cobaltocenium containing monomers and their polymers. Methods of polymerizing the cobaltocenium containing monomers are also provided along with their methods of use. Each cobaltocenium containing monomer contains a cobaltocenium moiety covalently connected to a polymerizable group, either directly (i.e., without any atoms therebetween) or indirectly through a covalent linkage. For example, the cobaltocenium moiety can be covalently connected to a polymerizable group via an alkyl linkage, an alkene linkage, or other organic linkage etc. (e.g., having a length of from 2 carbons to 12 carbons). In one particular embodiment, for example, the cobaltocenium moiety can be covalently connected to a polymerizable group via an ester group adjacent to the cobaltocenium moiety and/or an alkyl group between the ester group and the polymerizable group. Thus, cobaltocenium is attached as the side groups of the monomers and their resulting polymers.

The polymerizable group on the cobaltocenium containing monomer can be any suitable group capable of being polymerized. More particularly, methods are provided for preparing cobaltocenium containing polymers via polymerization of the cobaltocenium containing monomers (e.g., acrylate monomers, methacrylate monomers, styrene monomers, acrylamide monomers, norbornene monomers, caprolactone monomers, glycolide monomers, or mixtures thereof) to form a polymer (e.g., a homopolymer, random copolymer, and/or block copolymer). The polymer (e.g., homopolymer, random copolymer, and/or block copolymer) can have any suitable linkage between the polymer backbone and the cobaltocenium moiety. Compared with main-chain polymers, it is much easier to tune the polymer structures of side-chain polymers by changing the monomer structures.

Other monomers (e.g., non-cobaltocenium-containing monomers) can also be included in the polymers/copolymers to control the density of the cobaltocenium moieties in the resulting polymers/copolymers. As such, polymer compositions include homopolymers, random copolymers, and/or block copolymers. These polymers have cationic cobaltocenium moiety at the side-chain.

Thus, this embodiment provides an entirely new approach to synthesis of cobaltocenium containing monomers and side-chain cobaltocenium-containing polymers in applications such as redox sensors, molecular recognition, high-temperature resistance materials, catalysts, nanolithography, precursors for ceramics and magnetic materials, anti-proliferation reagents, etc. As polyelectrolytes, side-chain cobaltocenium-containing polymers can be used as coatings, controlled drug delivery, gene delivery and other biomedical applications.

As such, the presently disclosed methods can offer the following key features: (1) cobaltocenium can be integrated as part of monomer units; (2) cobaltocenium-containing monomers can be used for preparation of side-chain cobaltocenium-containing polymers (e.g., side-chain cobaltocenium-containing homopolymers, side-chain cobaltocenium-containing random copolymers, side-chain cobaltocenium-containing block copolymers; etc.; including copolymers including other types of monomers); (3) other monomers (e.g., non-cobaltocenium-containing monomers) can also be included in the (co)polymers to control the density of the cobaltocenium moieties in the resulting (co)polymers. As such, polymer compositions include homopolymers, random copolymers, and/or block copolymers. Additionally, cobaltocenium—can be attached to side chains of the polymer via any suitable linkage or functionalization. The counter ions can be exchanged via ion exchange in the side-chain cobaltocenium-containing polymers and/or monomers.

After polymerization, ion exchange of the cobaltocenium containing polymers can be used to change the anions associated with cationic cobaltocenium moiety. For example, the anions to be included in the cationic cobaltocenium moiety can include but are not limited to hydroxyl ($OH^-$), halide (chloride, bromide, fluoride), nitrate ($NO_3^-$), hexafluorophosphate ($PF_6^-$), tetraphenylborate ($BPh_4^-$), etc. or mixtures thereof.

The properties of cobaltocenium polymers can also be tuned by changing the monomer structures, compositions of random copolymers and the anions, molecular weight of the polymer, etc.

I. Polymerization Techniques

As stated, the cobaltocenium containing polymers can be formed via controlled polymerizations, such as controlled radical polymerizations (CRPs) or controlled ring-opening polymerizations, which may be selected based upon the particular polymerizable group monomers and/or desired properties of the polymeric chains formed. Through the use of these controlled polymerizations, each polymer can be produced with low polydispersity and diverse architectures. Thus, these methods are ideal for block polymer and/or graft polymer synthesis.

Controlled radical polymerization generally refers to chain growth polymerization which proceeds with significantly suppressed termination or chain transfer steps. Thus, polymerization in CRP proceeds until all monomer units have been consumed or until the reaction is terminated (e.g., through quenching and/or deactivating), and the addition of monomer results in continued polymerization, making CRP ideal for block polymer and graft polymer synthesis. The molecular weight of the resulting polymer is generally a linear function of conversion so that the polymeric chains are initiated and grow substantially uniformly. Thus, CRPs provide precise control on molecular structures, functionality and compositions. Thus, these polymers can be tuned with desirable compositions and architectures.

Controlled radical polymerizations can be used to produce block copolymers because CRP can leave a functional terminal group on the polymer formed (e.g., a halogen functional group). For example, in the copolymerization of two monomers (A and B) allowing A to polymerize via CRP will exhaust the monomer in solution with minimal termination. After monomer A is fully reacted, the addition of monomer B will result in a block copolymer. Controlled ring-opening polymerizations can utilize suitable catalysts such as tin(II) to open the rings of monomers to form a polymer.

Several of such polymerization techniques are discussed in this application. These techniques are generally known to those skilled in the art. A brief general description of each technique is below, and is provided for further understanding of the present invention, and is not intended to be limiting:

A. Reversible Addition-Fragmentation Chain Transfer Polymerization

Reversible Addition-Fragmentation chain Transfer polymerization (RAFT) is one type of controlled radical polymerization. RAFT polymerization uses thiocarbonylthio compounds, such as dithioesters, dithiocarbamates, trithiocarbonates, and xanthates, in order to mediate the polymerization via a reversible chain-transfer process. RAFT polymerization can be performed by simply adding a chosen quantity of appropriate RAFT agents (thiocarbonylthio compounds) to a conventional free radical polymerization. RAFT polymerization is particularly useful with monomers having a vinyl functional group (e.g., a (meth)acrylate group).

Typically, a RAFT polymerization system includes the monomer, an initiator, and a RAFT agent (also referred to as a chain transfer agent). Because of the low concentration of the RAFT agent in the system, the concentration of the initiator is usually lower than in conventional radical polymerization. Suitable radical initiators can be azobisisobutyronitrile (AIBN), 4,4'-azobis(4-cyanovaleric acid) (ACVA), etc.

RAFT agents are generally thiocarbonylthio compounds, such as generally shown below:

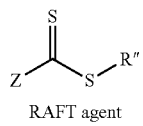

RAFT agent where the z group primarily stabilizes radical species added to the C=S bond and the R group is a good homolytic leaving group which is able to initiate monomers. For example, the z group can be an aryl group (e.g., phenyl group, benzyl group, etc.), an alkyl group, etc. The R" group can be an organic chain terminating with a carboxylic acid group.

As stated, RAFT is a type of living polymerization involving a conventional radical polymerization in the presence of a reversible chain transfer reagent. Like other living radical polymerizations, there is minimized termination step in the RAFT process. The reaction is started by radical initiators (e.g., AIBN). In this initiation step, the initiator reacts with a monomer unit to create a radical species which starts an active polymerizing chain. Then, the active chain reacts with the thiocarbonylthio compound, which kicks out the homolytic leaving group (R"). This is a reversible step, with an intermediate species capable of losing either the leaving group (R") or the active species. The leaving group radical then reacts with another monomer species, starting another active polymer chain. This active chain is then able to go through the addition-fragmentation or equilibration steps. The equilibration keeps the majority of the active propagating species into the dormant thiocarbonyl compound, limiting the possibility of chain termination. Thus, active polymer chains are in equilibrium between the active and dormant species. While one polymer chain is in the dormant stage (bound to the thiocarbonyl compound), the other is active in polymerization.

By controlling the concentration of initiator and thiocarbonylthio compound and/or the ratio of monomer to thiocarbonylthio compound, the molecular weight of the polymeric chains can be controlled with low polydispersities.

Depending on the target molecular weight of final polymers, the monomer to RAFT agent ratios can range from about less than about 10 to more than about 1000 (e.g., about 10 to about 1,000). Other reaction parameters can be varied to control the molecular weight of the final polymers, such as solvent selection, reaction temperature, and reaction time. For instance, solvents can include conventional organic solvents such as tetrahydrofuran, toluene, dimethylformamide, anisole, acetonitrile, dichloromethane, etc. The reaction temperature can range from room temperature (e.g., about 20° C.) to about 120° C. The reaction time can be from less than about 1 h to about 48 h.

The RAFT process allows the synthesis of polymers with specific macromolecular architectures such as block, gradient, statistical, comb/brush, star, hyperbranched, and network copolymers.

Because RAFT polymerization is a form of living radical polymerization, it is ideal for synthesis of block copolymers. For example, in the copolymerization of two monomers (A and B) allowing A to polymerize via RAFT will exhaust the monomer in solution with significantly suppressed termination. After monomer A is fully reacted, the addition of monomer B will result in a block copolymer. One requirement for maintaining a narrow polydispersity in this type of copolymer is to have a chain transfer agent with a high transfer constant to the subsequent monomer (monomer B in the example).

Using a multifunctional RAFT agent can result in the formation of a star copolymer. RAFT differs from other forms of CRPs because the core of the copolymer can be introduced by functionalization of either the R group or the Z group. While utilizing the R group results in similar structures found using ATRP or NMP, the use of the Z group makes RAFT unique. When the Z group is used, the reactive polymeric arms are detached from the core while they grow and react back into the core for the chain-transfer reaction.

B. Atom Transfer Radical Polymerization

Atom transfer radical polymerization (ATRP) is another example of a living radical polymerization. The control is achieved through an activation-deactivation process, in which most of the reaction species are in dormant format, thus significantly reducing chain termination reaction. The four major components of ATRP include the monomer, initiator, ligand, and catalyst. ATRP is particularly useful monomers having a vinyl functional group (e.g., a (meth)acrylate group).

Organic halides are particularly suitable initiators, such as alkyl halides (e.g., alkyl bromides, alkyl chlorides, etc.). For instance, in one particular embodiment, the alkyl halide can be ethyl 2-bromoisobutyrate. The shape or structure of the initiator can also determine the architecture of the resulting polymer. For example, initiators with multiple alkyl halide groups on a single core can lead to a star-like polymer shape.

The catalyst can determine the equilibrium constant between the active and dormant species during polymerization, leading to control of the polymerization rate and the equilibrium constant. In one particular embodiment, the catalyst is a metal having two accessible oxidation states that are separated by one electron, and a reasonable affinity for halogens. One particularly suitable metal catalyst for ATRP is copper (I).

The ligands can be linear amines or pyridine-based amines.

Depending on the target molecular weight of final polymers, the monomer to initiator ratios can range from less than about 10 to more than about 1,000 (e.g., about 10 to about 1,000). Other reaction parameters can be varied to control the molecular weight of the final polymers, such as solvent selection, reaction temperature, and reaction time. For instance, solvents can include conventional organic solvents such as tetrahydrofuran, toluene, dimethylformamide, anisole, acetonitrile, dichloromethane, etc. The reaction temperature can range from room temperature (e.g., about 20° C.) to about 120° C. The reaction time can be from less than about 1 h to about 48 h.

C. Nitroxide-Mediated Polymerization

Nitroxide-mediated polymerization (NMP) is another form of controlled living polymerization utilizing a nitroxide radical, such as shown below:

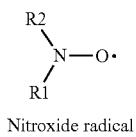

Nitroxide radical where R1 and R2 are, independently, organic groups (e.g., aryl groups such as phenyl groups, benzyl groups, etc.; alkyl groups, etc.). NMP is particularly useful with monomers having a vinyl functional group (e.g., a (meth)acrylate group).

D. Ring-Opening Metathesis Polymerization

Ring-opening metathesis polymerization (ROMP) is a type of olefin metathesis polymerization. The driving force of the reaction is relief of ring strain in cyclic olefins (e.g. norbornene or cyclopentene) in the presence of a catalyst. The catalysts used in a ROMP reaction can include a wide variety of metals and range from a simple $RuCl_3$/alcohol mixture to Grubbs' catalyst.

In this embodiment, the monomer can include a strained ring functional group, such as a norbornene functional group, a cyclopentene functional group, etc. to form the polymeric chains. For example, norbornene is a bridged cyclic hydrocarbon that has a cyclohexene ring bridged with a methylene group in the para position.

The ROMP catalytic cycle generally requires a strained cyclic structure because the driving force of the reaction is relief of ring strain. After formation of the metal-carbene species, the carbene attacks the double bond in the ring structure forming a highly strained metallocyclobutane intermediate. The ring then opens giving the beginning of the polymer: a linear chain double bonded to the metal with a terminal double bond as well. The new carbene reacts with the double bond on the next monomer, thus propagating the reaction.

E. Ring-Opening Polymerization

In one particular embodiment, where the monomer includes a strained ring function group (e.g., a caprolactone or lactide), ring-opening polymerization (ROP) may be used to form the polymeric chain. For example, a caprolactone-substituted monomer is a polymerizable ester, which can undergo polymerization with the aid of an alcohol as an initiator and a tin-based reagent as a catalyst.

II. Cobaltocenium-Containing Vinyl Monomers and their Polymers

In one particular embodiment, for example, the polymerizable group can include a vinyl group (i.e., cobaltocenium vinyl monomers). Particularly suitable cobaltocenium vinyl monomers include but are not limited to acrylic, methacrylic, styrenic, or acrylamide monomers. As stated, diverse linkers (when present) can be placed between the vinyl groups and cobaltocenium groups.

Referring to FIG. 1, exemplary cobaltocenium vinyl monomers are shown, labeled 1-5. Monomer 1 shows a cobaltocenium moiety attached to an acrylate group (as the polymerizable group). In monomer 1, an ester group and a 2-C alkyl group (i.e., —$CH_2CH_2$—) forms a linkage between the cobaltocenium moiety and the acrylate group. Monomer 2 shows cobaltocenium moiety attached to a methacrylate group (as the polymerizable group). In monomer 2, an ester group and a 2-C alkyl group (i.e., —$CH_2CH_2$—) forms a linkage between the cobaltocenium moiety and the methacrylate group. Monomer 3 shows a cobaltocenium moiety attached to a styrene group (as the polymerizable group). In monomer 3, an ester group forms a linkage between the cobaltocenium moiety and the styrene group. Monomer 4 shows a cobaltocenium moiety attached to an acrylamide group (as the polymerizable group). In monomer 4, the cobaltocenium moiety is directly bonded to the acrylamide group. Monomer 5 shows a cobaltocenium moiety attached to an acryloyl group (as the polymerizable group). In monomer 5, the cobaltocenium moiety is bonded to the acryloyl group through R, wherein R can be a covalent bond, amine group, thiol group, an organic group (e.g., hydrocarbon), oxygen-containing linkage (e.g., —O—, an ester group, etc.), or a combination thereof.

Cobaltocenium-containing polymers be prepared from such cobaltocenium vinyl monomers according to any suitable process, such as via radical polymerization, to form side-chain cobaltocenium-containing polymers of polyacrylates, polymethacrylates, polystyrenes, polyacrylamides, polyacryloyls, etc., or mixtures or copolymers thereof. Other monomers (e.g., non-cobaltocenium-containing monomers) can also be included in the (co)polymers to control the density of the cobaltocenium moieties in the resulting (co)polymers. As such, polymer compositions include homopolymers, random copolymers, and/or block copolymers. These polymers have cationic cobaltocenium moiety at the side-chain. The counter ions or anions can be hydroxyl ($OH^-$), halide (chloride, bromide, fluoride), nitrate ($NO^{3-}$), hexafluorophosphate ($PF_6^-$), tetraphenylborate ($BPh_4^-$), etc.

In one particular embodiment, polymerization of the cobaltocenium vinyl monomers can be achieved through RAFT polymerization, as generally described above.

III. Ring-Opening Metathesis Polymerization

In one particular embodiment, cobaltocenium-containing cationic polyelectrolyte polymers can be formed via ring-opening metathesis polymerization (ROMP), as generally described above. For example, a cobaltocenium-containing norbornene monomer (where the polymerizable group comprises a norbornene group) can be polymerized via ROMP, such as the exemplary cobaltocenium-containing norbornene monomer 6 shown in FIG. 1. Other linkers can be included, such as different alkyl chains, etc. Norbornene carboxylic acid can be also used to prepare cobaltocenium-containing norbornene monomer with different linkers.

IV. Ring-Opening Polymerization

In one particular embodiment, cobaltocenium-containing cationic polyelectrolyte polymers can be formed via ring-opening polymerization (ROP), as generally described above. For example, a cobaltocenium-containing caprolactone monomer 7 (FIG. 1, where the polymerizable group comprises a caprolactone group) can be polymerized via ROP. Other linkers can be included, such as different alkyl chains, etc. Lactide can be also used as the substrate to prepare cobaltocenium-containing glycolide monomer with different linkers.

EXAMPLES

Examples of such cobaltocenium containing monomers and their polymers are described below. This work shows the potential for many other polymer systems to be applied in a similar fashion to obtain controlled properties. The strategy described here not only offers the diversity of structures of different monomer and polymer systems, but also tailored properties. The successful implementation of this strategy will enable side-chain cobaltocenium polymers with novel properties.

Example 1

Synthesis and Polymerization of Cobaltocenium Vinyl Monomers

Figure 2:
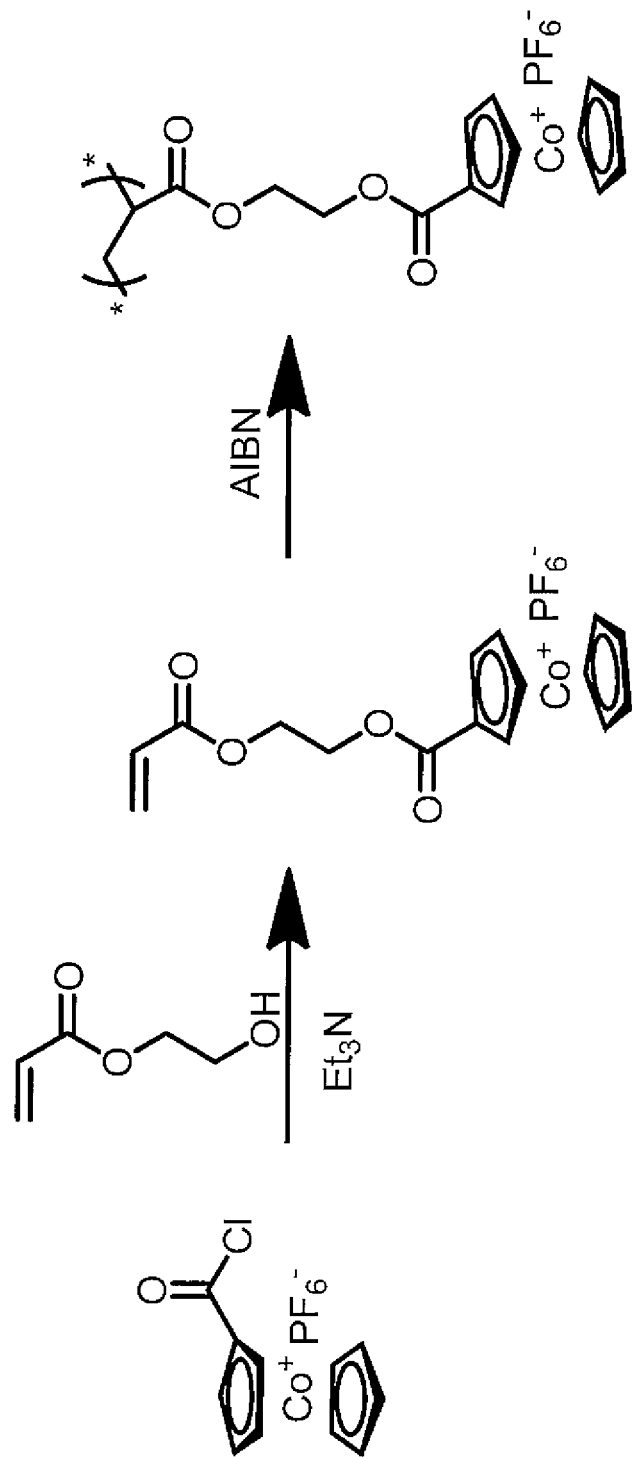
FIG. 2 shows an example of preparation of a cobaltocenium acrylic monomer, 2-acryloyloxyethyl cobaltocenium-carboxylate hexafluorophosphate (AECoPF6), and its cobaltocenium homopolymer.

The synthesis of cobaltocenium vinyl monomers was demonstrated. The monomers include acrylic, methacrylic, styrenic and acrylamide monomers. FIG. 1 illustrates exemplary cobaltocenium vinyl monomers, with vinyl monomers with cobaltocenium at the end of pedant group. The linkers between cobaltocenium and vinyl groups have different lengths ranging from 2 carbons to 12 carbons. For example, 2-acryloyloxyethyl cobaltoceniumcarboxylate hexafluorophosphate ($AECoPF_6$) is prepared by esterification reaction between mono-substituted cobaltocenium acyl chloride and 2-hydroxyethyl acrylate in the presence of triethylamine, as shown in FIG. 2.

The synthesis of side-chain cobaltocenium-containing polymers was demonstrated. For example, $AECoPF_6$ homopolymers were prepared by free radical polymerization of $AECoPF_6$ monomers in the presence of azoisobutyronitrile (AIBN) as illustrated in FIG. 2. The absolute molecular weight of this polymer can be as high as 200,000 g/mol. These polymers can be tuned by changing the linkers between cobaltocenium and vinyl groups as demonstrated in above.

Figure 3:
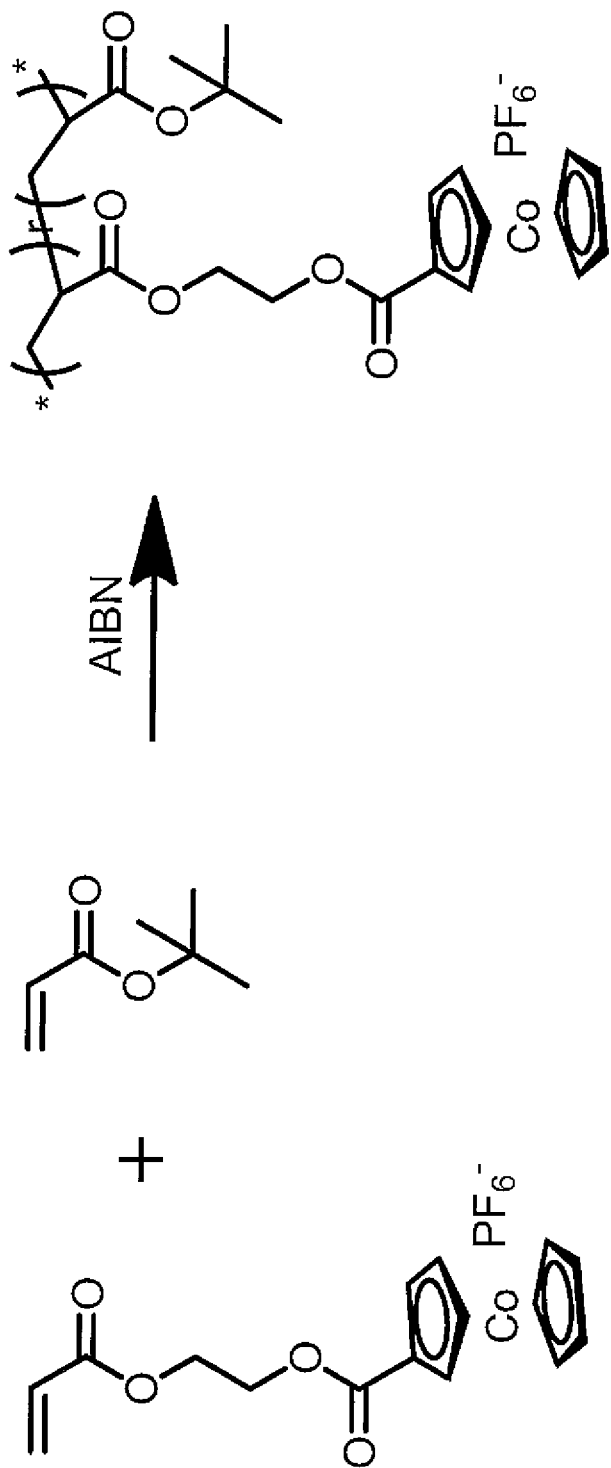
FIG. 3 is an example of a side-chain cobaltocenium-containing random copolymer prepared by free radical polymerization of AECoPF6 and tBA.

The synthesis of side-chain cobaltocenium-containing random copolymers was also demonstrated. For example, poly (2-acryloyloxyethyl cobaltoceniumcarboxylate hexafluorophosphate)-r-poly(tert-butyl acrylate) were prepared via free radical polymerization of $AECoPF_6$ and tert-butyl acrylate (tBA) together initiated by AIBN. These random copolymers can be tuned with different compositions. The tBA unit can be replaced by other units, e.g. methyl methacrylate, butyl acrylate, styrene, 4-chloride styrene, 2-hydroxyethyl methacrylate, isopropyl acrylamide, etc. This method involves a polymeric composition comprising different cobaltocenium fraction. FIG. 3 illustrates a scheme for one particular embodiment—the case of random copolymers of PtBA and $PAECoPF_6$.

Figure 4:
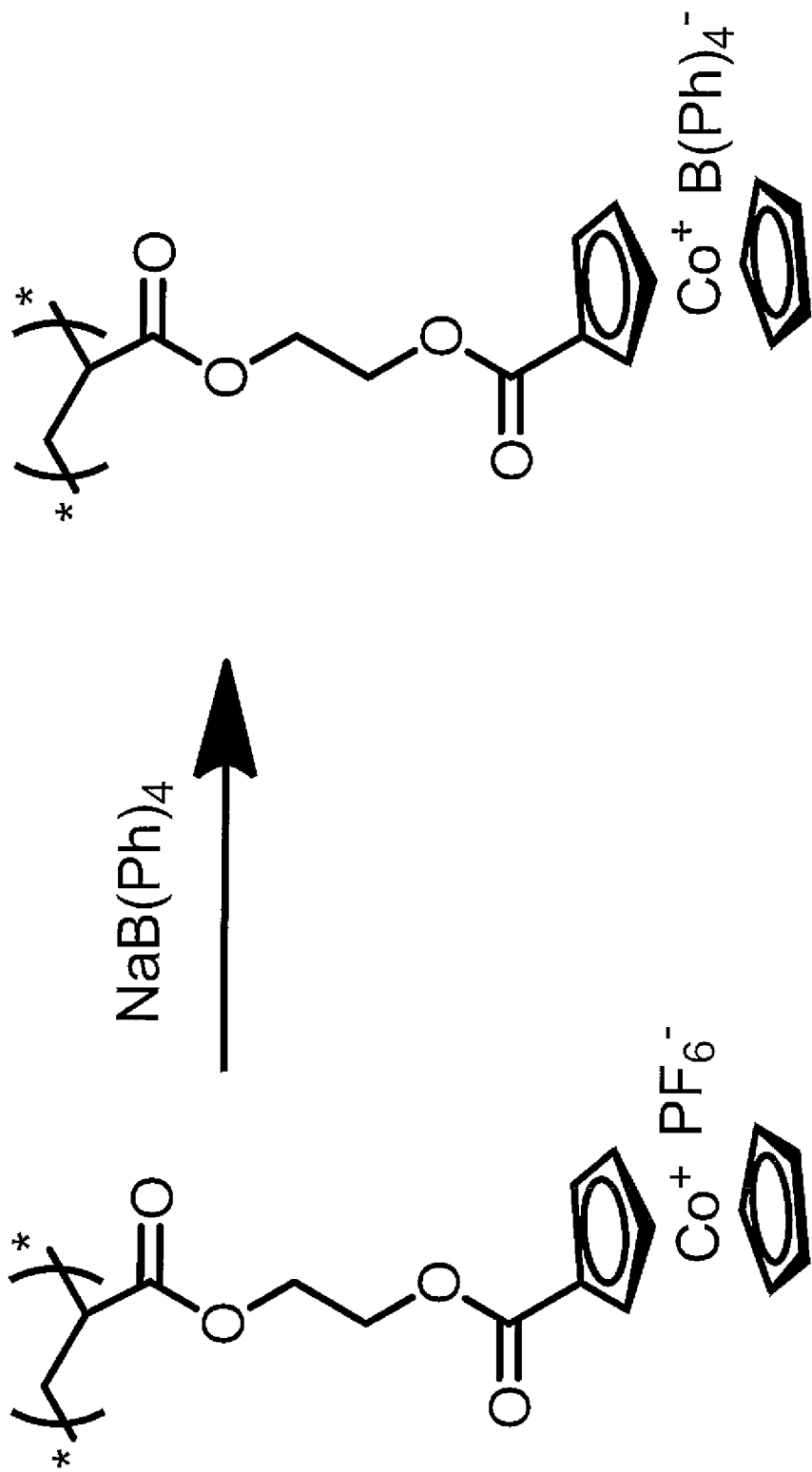
FIG. 4 is an example of ion exchange of cobaltocenium polymers from $PF_6^-$ to $B(Ph)_4^-$.

An ion exchange of cobaltocenium polymers to change the anions associated with cationic cobaltocenium moiety was demonstrated. The anions include hydroxyl ($OH^-$), halide (chloride, bromide, fluoride), nitrate ($NO_3^-$), hexafluorophosphate ($PF_6^-$), tetraphenylborate ($BPh_4^-$) and so on. FIG. 4 shows the ion exchange from $PF_6^-$ to $BPh_4^-$, as an exemplary method. The anion is exchanged by adding sodium tetraphenylborate in aqueous solution. The polymers with $BPh_4^-$ precipitate out of the solution. Also, the ion exchange can be achieved with the aid of anionic ion-exchange resins.

Example 1A

Cobaltocenium vinyl monomers were prepared as shown in FIG. 2. A typical procedure for the synthesis is described as follows: 2-hydroxyethyl acrylate and mono-substituted cobaltocenium acyl chloride were dissolved in tetrahydrofuran, followed by adding triethylamine dropwise under the protection of nitrogen gas. The mixture was stirred at room temperature for 48 h to yield 2-acryloyloxyethyl cobaltoceniumcarboxylate hexafluorophosphate ($AECoPF_6$).

Example 1B

Cobaltocenium homopolymers were prepared using the monomers of Example 1A as shown in FIG. 2. The monomers were polymerized by free radical polymerization using AIBN as initiators. The polymerization of $AECoPF_6$ was carried out by the following procedures: in a dry Schlenk flask, $AECoPF_6$ and AIBN were dissolved in acetonitrile and followed by purging with nitrogen gas. The mixture was heated at 90° C. for 30 h to yield cobaltocenium homopolymers (FIG. 2).

Example 1C

Cobaltocenium random copolymers, $PAECoPF_6$-r-PtBA, were prepared as shown in FIG. 3 using the monomers of Example 1A. The procedures were similar to Example 1B as follows: in a dry Schlenk flask, tBA, $AECoPF_6$ and AIBN were dissolved in acetonitrile and followed by purging with nitrogen gas. The mixture was stirred at 90° C. for 6 h to yield $AECoPF_6$ and tBA random copolymers.

Example 1D

AECo polymers with $BPh_4^-$ as anions were prepared using the polymer of Example 1B. $NaBPh_4$ was dissolved in aqueous solution followed by adding $PAECoPF_6$ aqueous solution to yield polymer $PAECoBPh_4$.

Example 1E

AECo polymers with $Cl^-$ as anions were prepared using the polymer of Example 1B. $PAECoPF_6$ was mixed with an anion exchange resin of chloride for 24 h, yielding polymer PAECoCl.

Example 2

Synthesis and Polymerization of Cobaltocenium-Containing Caprolactone Monomers

A cobaltocenium carboxylic acid was reacted with allyl alcohol in the presence of triethylamine to obtain cobaltocenium allyl ester, which was further reacted with much excess 1,2-dithiolethylene. A thiol-containing cobaltocenium was obtained. α-Allyl-ε-caprolactone was reacted the thiol-containing cobaltocenium in the presence of AIBN through thiol-ene click reaction to provide monomer 7 shown in FIG. 1. The monomer 7 was then carried out ROP in the presence of benzyl alcohol and Sn(II) 2-ethylhexanoate at 120° C.

Example 3

Synthesis and Polymerization of Cobaltocenium-Containing Norbornene Monomers

A series of cobaltocenium-containing norbornene monomers were synthesized, which were initiated by Grubbs III catalyst to obtain cobaltocenium-containing homopolymers. The obtained number average molecular weight ($M_n$) was as high as 400,000 g/mol. One-pot two-step sequential ROMP was further used to prepare a variety of cobaltocenium-containing block copolymers. The self-assembly of amphiphilic cobaltocenium-containing block copolymers was explored and used them as templates to prepare discrete cobalt oxide nanoparticles. The anticancer studies indicated that water-soluble cobaltocenium polyelectrolytes exhibited antiproliferative activities on prostate cancer cells, while showing negligible toxicity on non-cancerous mesenchymal stem cells.

Figure 5:
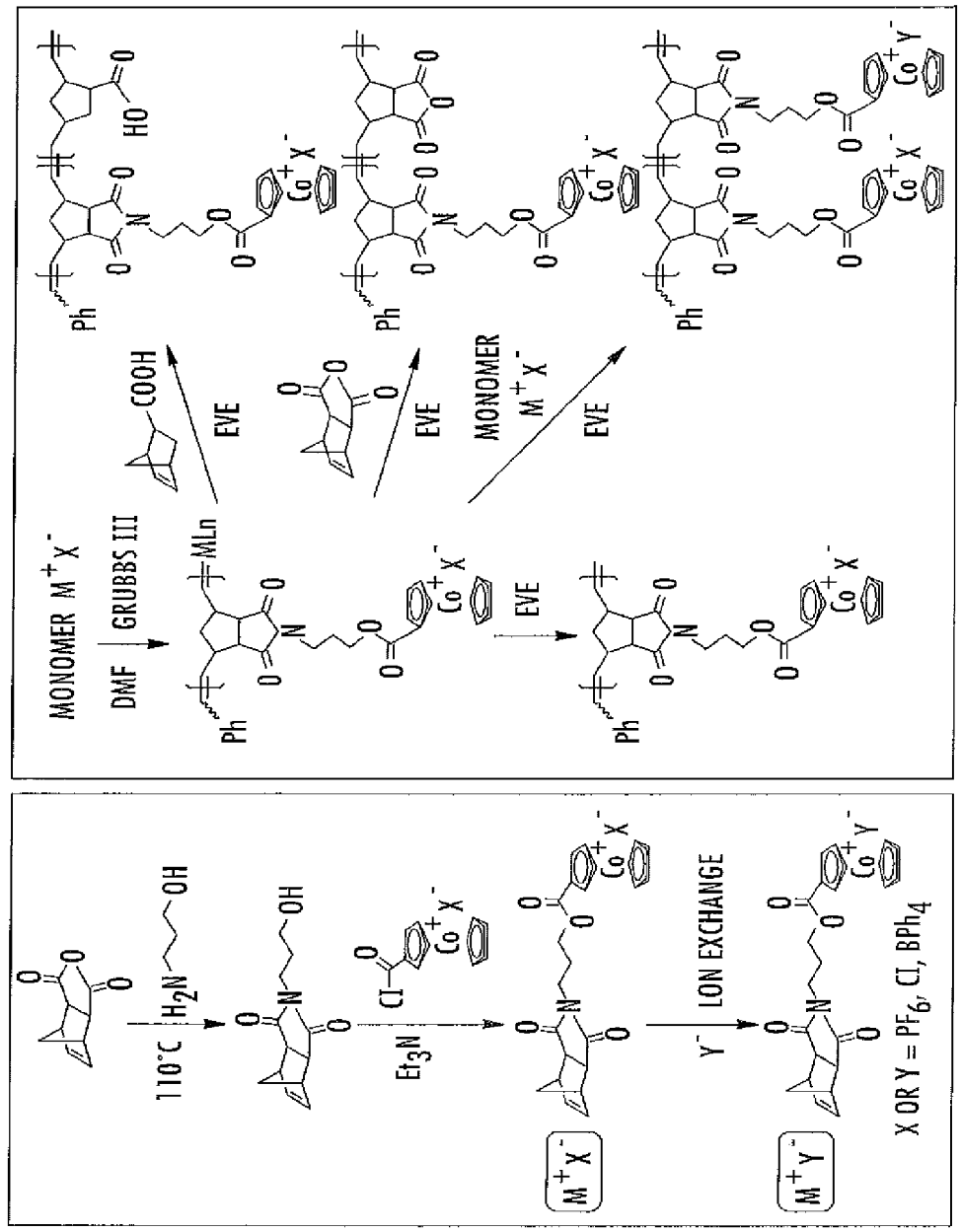
FIG. 5 shows the synthesis of cobaltocenium-containing norbornene monomers, cobaltocenium-containing homopolymers, and block copolymers via ROMP, according to one exemplary embodiment.
Figure 6A:
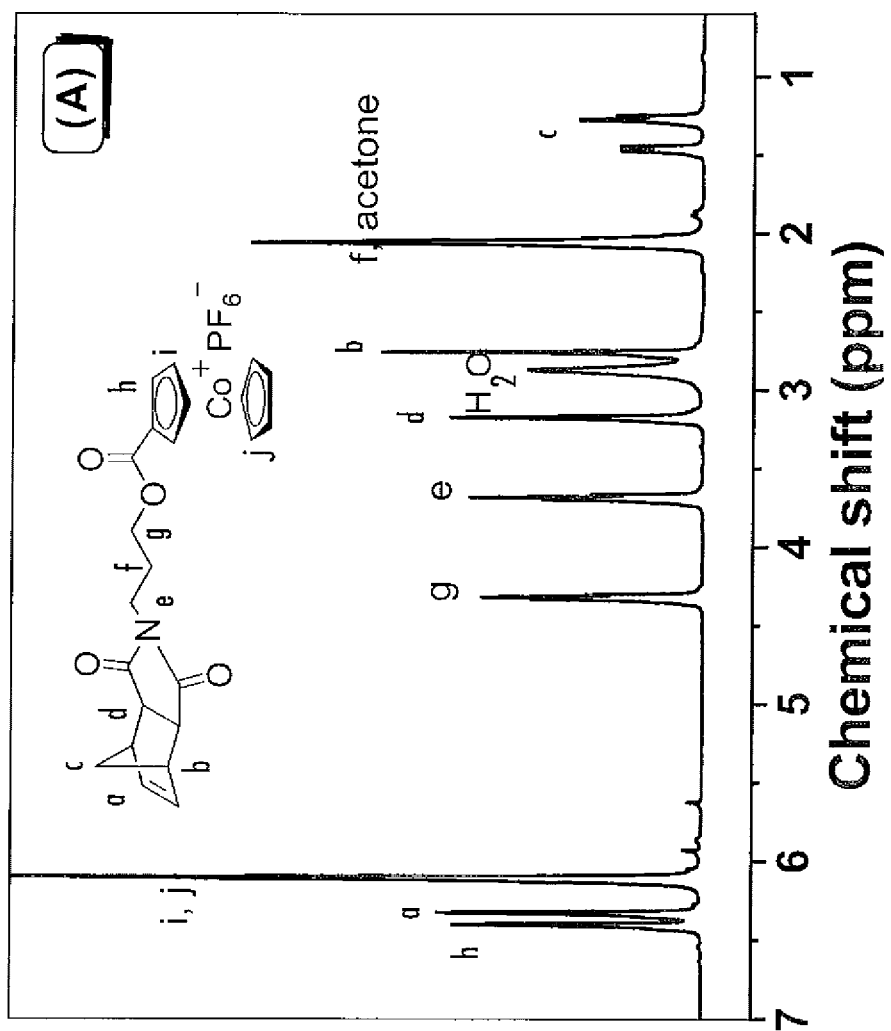
FIG. 6 shows the $^1H$ NMR spectra of (A) monomer MPF6 and (B) corresponding homopolymer PMPF6 prepared according to one Example.

As shown in FIG. 5, the cobaltocenium-containing norbornene-based monomer, N-[3-cobaltoceniumcarboxyl propyl]-cis-5-norbornene-exo-2,3-dicarboximide hexafluorophosphate (NCF6), was prepared by an esterification reaction between cobaltocenium acyl chloride and N-[3-hydroxylpropyl]-cis-5-norbornene-exo-2,3-dicarboximide (NPH) in the presence of triethylamine. NPH was prepared from cis-5-norbornene-exo-2,3-dicarboxylic anhydride in the presence of 3-amino-1-propanol at 110° C. FIG. 6A shows the $^1$H NMR spectrum of the NCPF6 monomer. The peak at 6.3 ppm corresponded to the vinyl protons, while the peaks at 6.4 ppm and 6.1 ppm originated from characteristic cyclopentadienyl (Cp) protons. Protons next to the imide and ester groups were located at 4.3 ppm and 3.7 ppm respectively. All other peaks were clearly assigned.

Due to the presence of negatively charged counter-ion $PF_6^-$ in the cobaltocenium monomer NCPF6, simple ion-exchange processes were carried out to convert $PF_6^-$ to $Cl^-$ and $BPh_4^-$, yielding cobaltocenium monomers NCCl and NCBPh4 respectively. The highly efficient quantitative ion-exchange was confirmed from the $^{19}$F NMR analyses. The typical doublet peak at ca. −75 ppm, corresponding to the P—F coupling of $PF_6^-$ group, completely disappeared after the ion-exchange in both monomer synthesis.

Figure 6B:
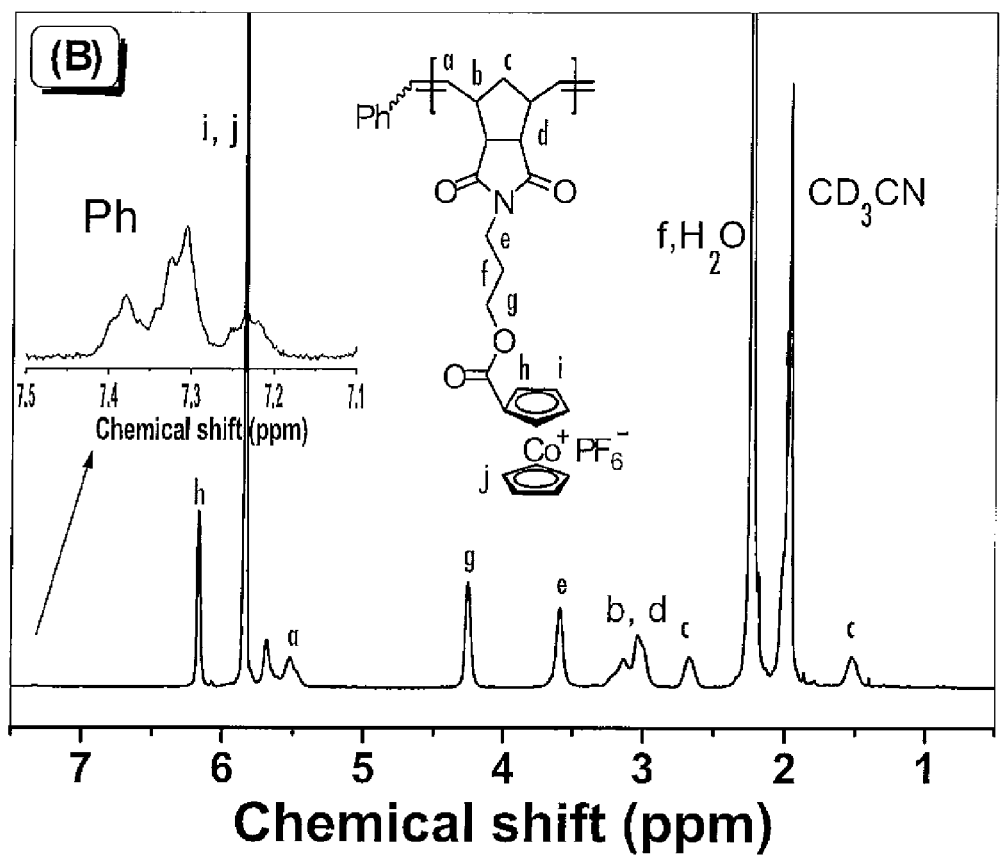

The synthesis of cobaltocenium-containing polyelectrolyte polymers by ROMP was performed as shown in FIG. 5. Table 1 summarized results of different side-chain cobaltocenium-containing homopolymers and block copolymers using Grubbs III catalyst. All reactions were conducted under open air at room temperature. The success of this polymerization was substantial given its rapidness and friendly reaction conditions. FIG. 6B shows $^1$H NMR spectrum of the resulting side-chain cobaltocenium-containing homopolymer, PNCPF6. Compared with the NCPF6 monomer, chemical shifts of vinyl protons on the polymer backbone moved to a higher field at 5.4-5.8 ppm with two broader peaks observed, which arose from the cis and trans conformations of the double bonds in the main chain. The signal of methylene protons of cyclopentane on the backbone revolved into two different peaks located at 1.5 ppm and 2.6 ppm. Cp protons had two signals at 5.85 ppm and 6.15 ppm, a shift toward a higher field, compared with those from the monomer. Peaks located at 7.2-7.5 ppm corresponded to the phenyl end group originating from the Grubbs III catalyst, which was also used to determine number average molecular weight of resulting polymers. The molecular weight determined by NMR was consistent with the theoretical value calculated from the feed molar ratios of monomer to catalyst.

TABLE 1

Side-chain Cobaltocenium-containing Polyelectrolyte Homopolymers and Block Copolymers.

| Polymer | [M1]:[M2]:[G3]$^a$ | DP$^b$ | $M_n$ (g/mol)$^c$ |
|---|---|---|---|
| PNCPF6 | 100:0:1 | 100 | 58,000 |
| PNCPF6-2 | 500:0:1 | 487 | 287,000 |
| PNCCl | 100:0:1 | 100 | 47,000 |
| PNCBPh4 | 100:0:1 | 100 | 64,000 |
| PNCPF6-b-PNCA | 50:50:1 | 50/50 | 24,000 |
| PNCPF6-b-PNDA | 50:50:1 | 50/50 | 37,000 |
| PNCPF6-b-PMCl | 50:50:1 | 50/50 | 52,000 |
| PNCPF6-b-PMBPh4 | 50:50:1 | 50/50 | 63,000 |
| PMCl-b-PNCBPh4 | 70:30:1 | 70/30 | 48,000 |
| PNPH | 100:0:1 | 100 | 22,000 |

Note.
$^a$the feed molar ratio of monomer to Grubbs III catalyst;
$^b$the degree of polymerization of homopolymers or each block in block copolymers calculated from $^1$H NMR by conversion.
$^c$the molecular weight calculated from $^1$H NMR by end group analysis.

Figure 7A:
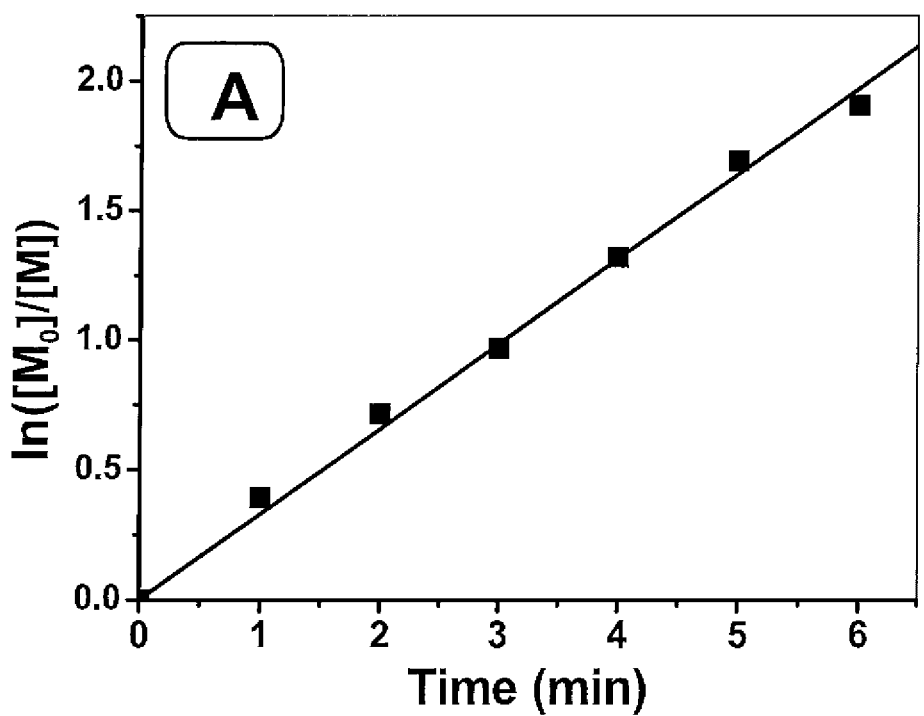
FIG. 7 shows the kinetic plots (A, B and C) of PMPF6 synthesis with the use of Grubbs III catalyst in dry DMF; Kinetic plot (D) of a chain-extension reaction to prepare PMPF6-b-PNCA block copolymers via one-pot two-step sequential ROMP according to one Example.
Figure 7B:
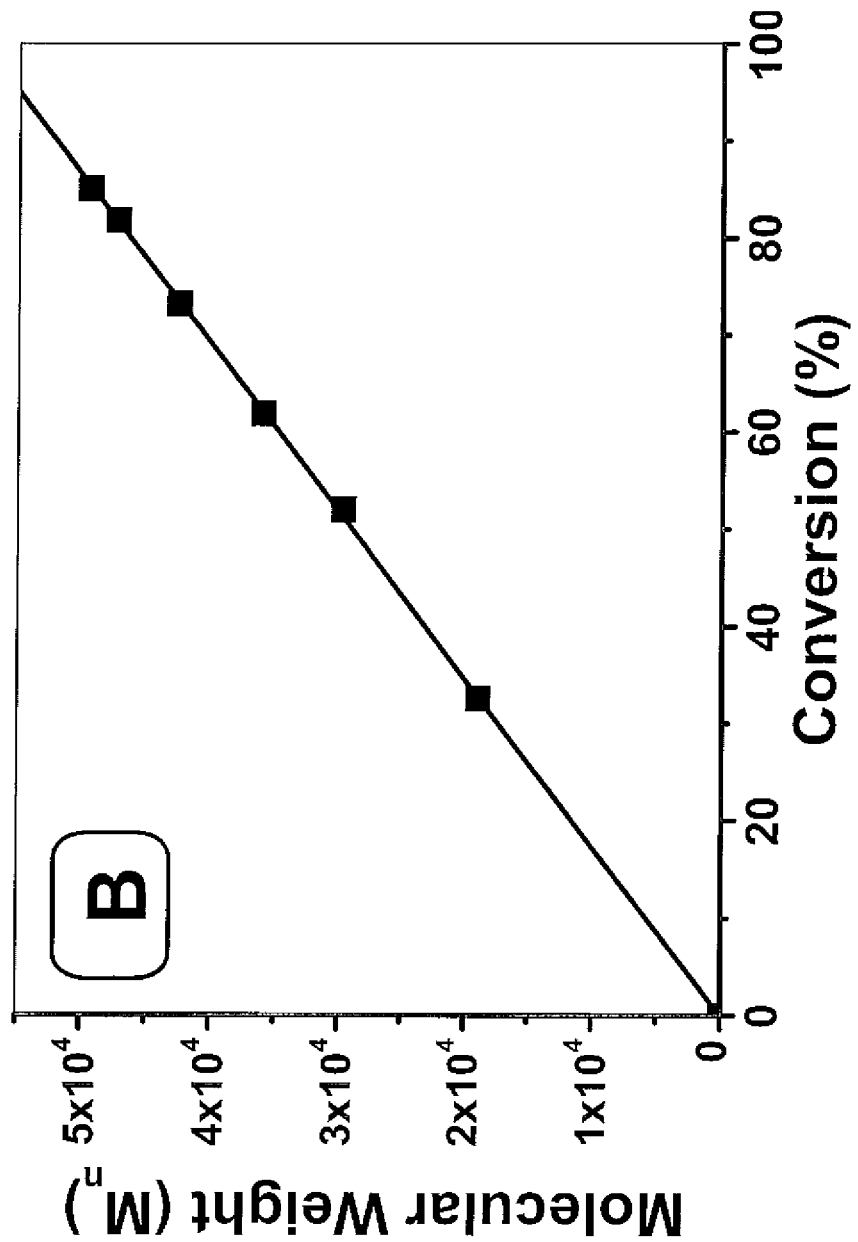
Figure 7C:
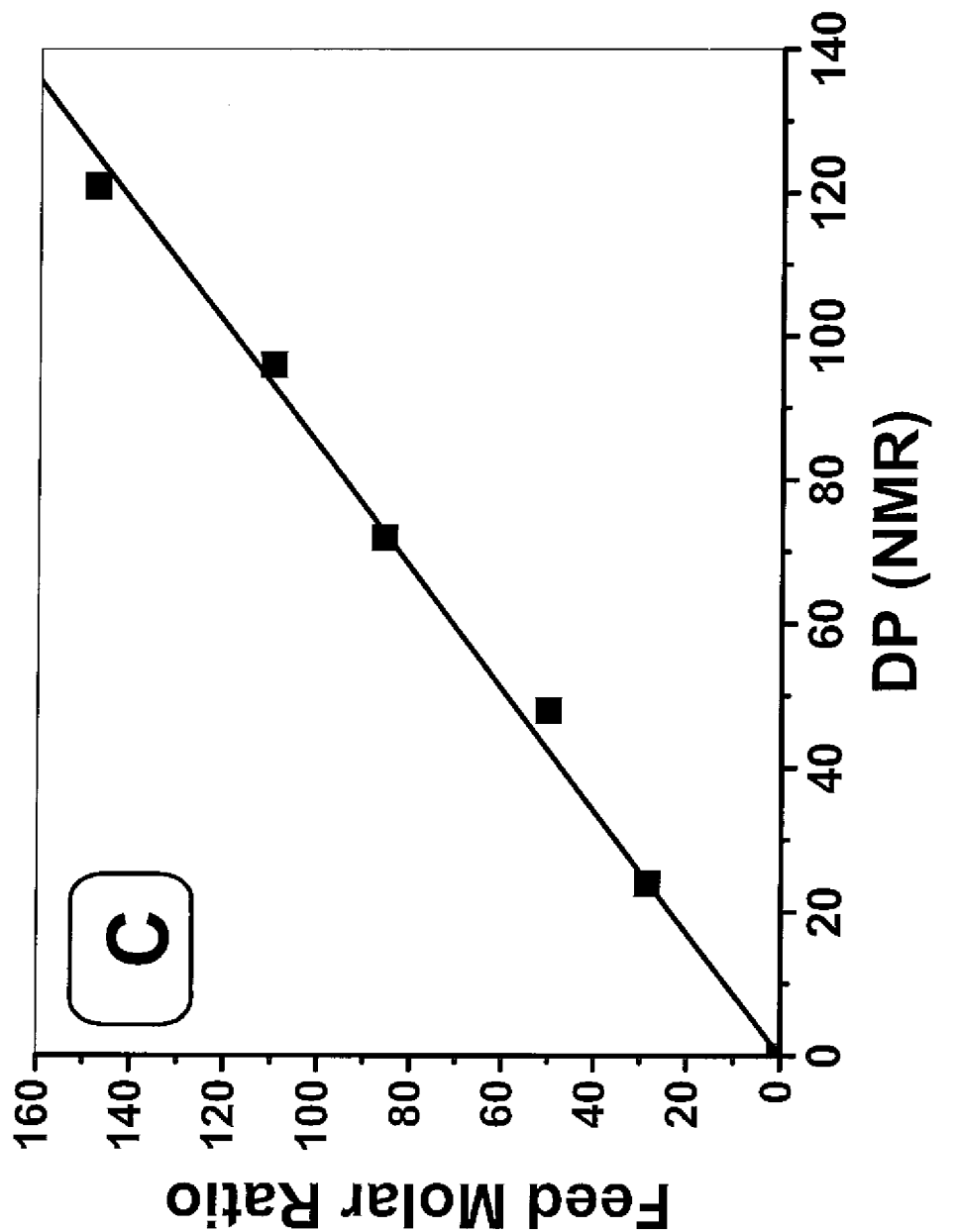

To explore whether the polymerization followed a living/controlled process, two different kinetic studies were performed. The first study was to take samples at predetermined intervals and stop the polymerization by instantaneous addition of EVE. The monomer conversions were calculated by comparing the $^1$H NMR signals of vinyl protons between monomers (6.3 ppm) and polymers (5.4-5.8 ppm). A semi-logarithmic plot was shown in FIG. 7A. A linear relationship between the reaction time and ln([M$_0$]/M) was obtained, clearly demonstrating the living characteristic of NCPF6 polymerization by ROMP. In parallel, molecular weight of the polymers determined by NMR end group analysis increased linearly with the monomer conversion (FIG. 7B). In a second study, a series of polymerization reactions with different molar feed ratios of monomer to catalyst were conducted with all monomer conversion reaching nearly 100%. Molecular weight of the polymers was obtained through NMR end-group analysis. FIG. 7C shows that molecular weight of final polymers increased linearly with the feed ratios, in excellent agreement with the theoretical molecular weight, another signature of a living polymerization. Thus, molecular weight of cobaltocenium-containing polymers can be facilely controlled by adjusting the reaction time and the feed ratio. Cobaltocenium-containing cationic polyelectrolytes with counter-ion $PF_6^-$ are not soluble in water, but soluble in acetonitrile (ACN), DMF and dimethylsulfoxide (DMSO).

Polymerizations of monomers NCCl and NCBPh4 were also successfully carried out with the aid of Grubbs III catalyst (Table 1). The solubility of PNCBPh4 was similar to PNCPF6, while PNCCl had a different solubility behavior. The PNCCl polymer is hydrophilic and soluble in methanol, water, DMF, ACN and DMSO.

Figure 7D:
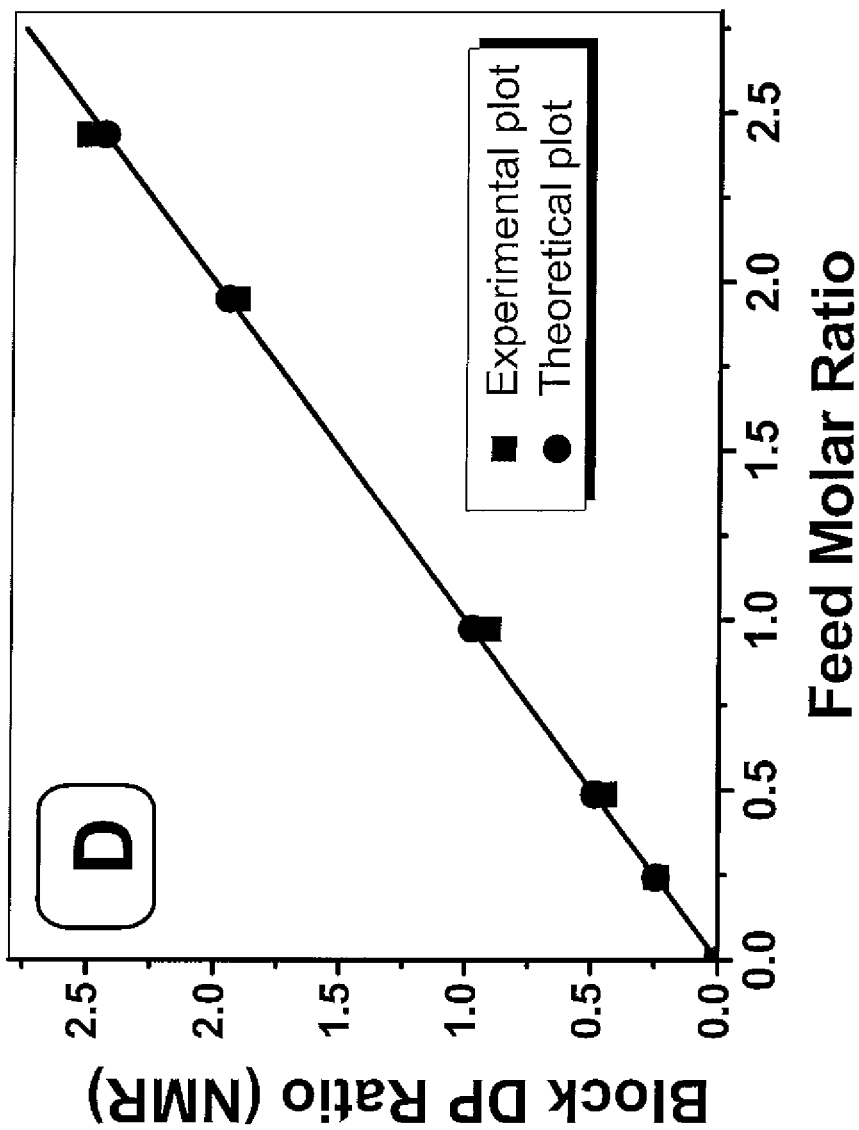

The living polymerization of cobaltocenium monomers further provided the possibility of macromolecular engineering toward cobaltocenium-containing polymers with diverse architectures. Well-defined side-chain cobaltocenium-containing cationic polyelectrolyte block copolymers were prepared via one-pot two-step sequential ROMP to chain-extend the first cobaltocenium-containing block to the second monomer. Two different block copolymers, PNCMPF6-b-poly(cis-5-norbornene-exo-2-carboxylic acid) (PNCPF6-b-PNCA) and PNCPF6-b-poly(cis-5-norbornene-exo-2,3-dicarboxylic anhydride) (PNCPF6-b-PNDA), were prepared. Chain-extension to either NCA or NDA was accomplished with nearly 100% monomer conversion. The $^1$H NMR spectrum of PNCPF6-b-PNCA showed a characteristic chemical shift at 12.0 ppm corresponded to the carboxyl proton. Comparison between the methylene protons (~1.5-1.8 ppm) from the cyclopentane backbone of the PNCA block and the vinyl protons (5.4-5.8 ppm) of the entire backbone of the block copolymer was used to determine compositions of two blocks. This calculation was in great agreement with the theoretical feed molar ratio of two monomers. A kinetic study of the block copolymer synthesis using PNCPF6 as the first block was conducted with different feed ratios of the second monomer, NCA, to the first macroinitiator PNCPF6. Based on the feed ratios and quantitative monomer conversion determined by NMR, the molecular weight of block copolymers had a linear relationship with the theoretical molecular weight, as shown in FIG. 7D. This kinetic study further demonstrated that the first cobaltocenium-containing block fully retained its end functional group, allowing for an efficient chain-extension in a controlled and living manner.

Given characteristic counter-ion dependent solubility of cobaltocenium, the synthesis of amphiphilic block copolymers with both blocks containing cobaltocenium moiety was performed, but with different counter-ions in each block (FIG. 5 and Table 1). Three block copolymers PNCPF6-b-PNCCl, PNCPF6-b-PNCBPh4, and PNCCl-b-PNCBPh4 were obtained by one-pot two-step ROMP with the aid of Grubbs III catalyst. Again, in-situ NMR analysis indicated that monomer conversion of the second block was nearly 100% for all block copolymer synthesis. The $^1$H NMR spectrum of PNCCl-b-PNCBPh4 ($^1$H NMR spectra of PNCPF6-b-PNCCl and PNCPF6-b-PNCBPh4 showed chemical shifts of cobaltocenium group and the main chain protons were maintained almost same for the PNCCl block and the PNCBPh4 block. By comparing the integration of peaks at 6.8-7.2 ppm (the phenyl group from $BPh_4^-$) and the peak at 6.2 ppm ($CH_2$ from all cobaltocenium groups), the molar ratio between the PNCCl block and the PNCBPh4 block can be calculated, which was consistent with the feed molar ratio of two monomers.

Figure 8A:
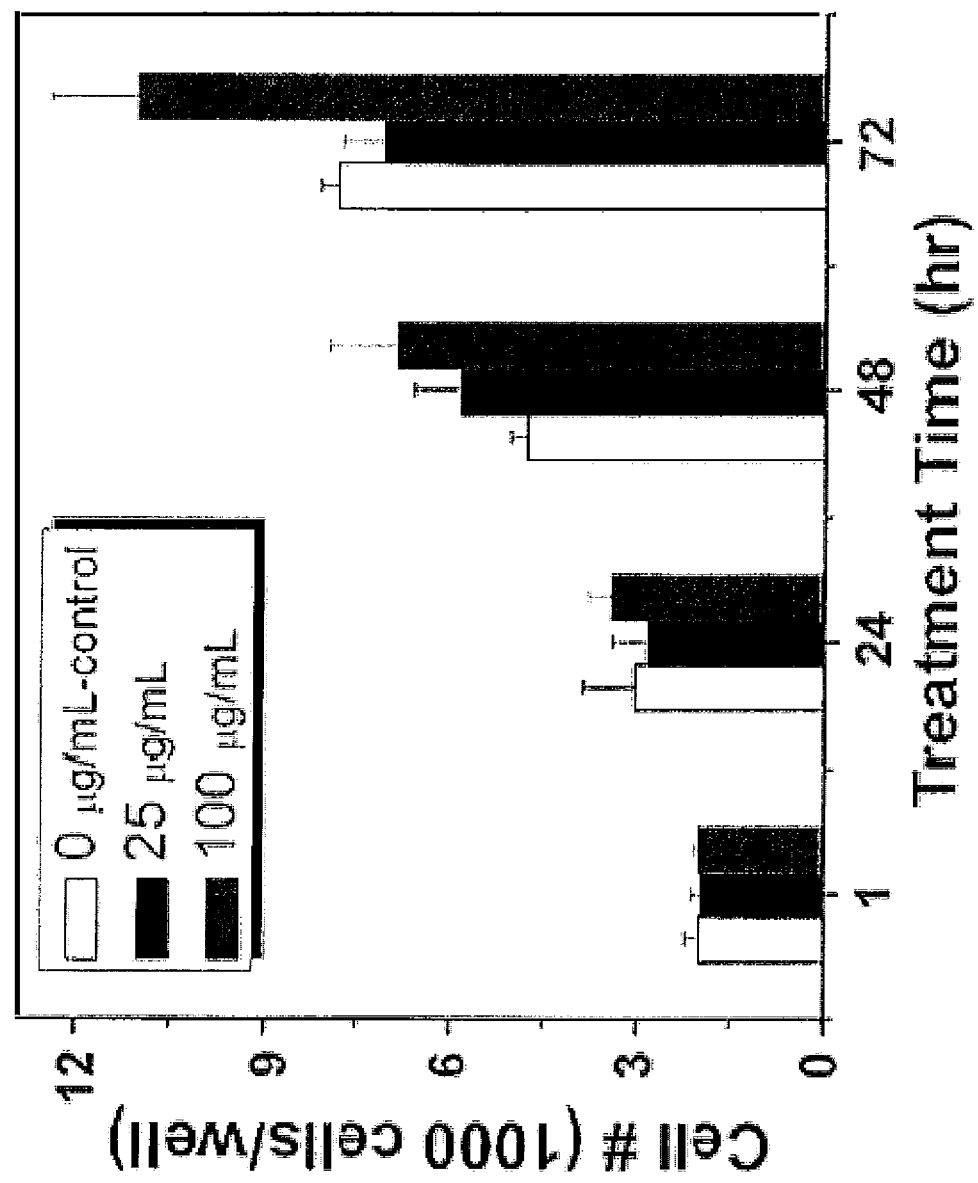
FIG. 8 shows quantitative data of cell proliferation after 72 hr incubation with PMCl according to the Examples.
Figure 8B:
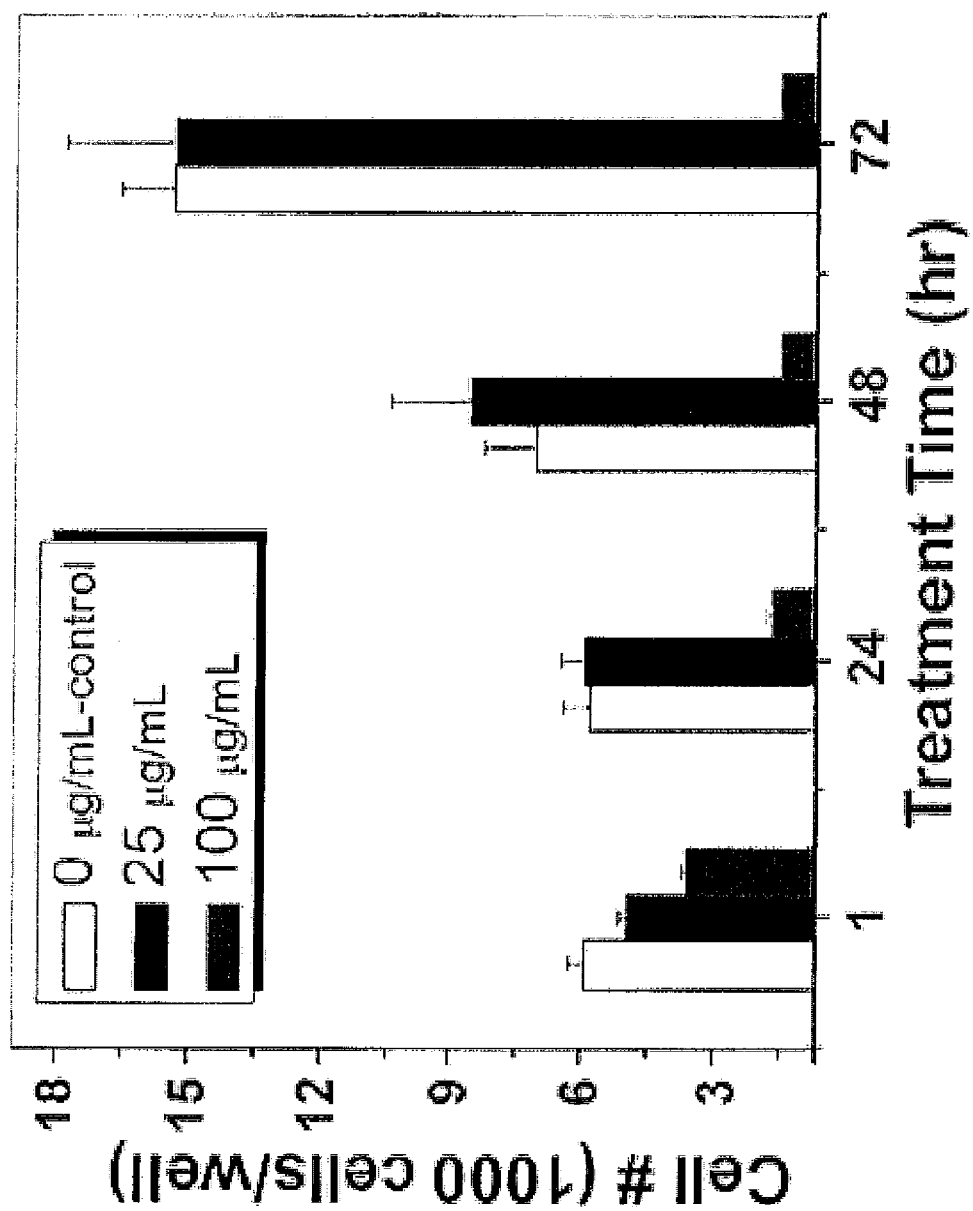

Anticancer activities of water-soluble cobaltocenium-containing polymers PNCCl were then tested. As demonstrated in a series, non-cancerous C3H10T1/2 mesenchymal stem cells incubated with PNCCl retained the same phenotypical (spindlelike) morphology as the control cells (cultured in regular medium without PNCCl). Moreover, mesenchymal stem cells cultured with the polymer at concentrations as high as 100 μg/ml proliferated to confluence in 72 h (3 days) similarly to the control cells. The qualitative observation was further confirmed by the quantitative data of the cell proliferation after 72 hr incubation with PNCCl shown in FIG. 8A. Interestingly, the polymer at a concentration of 100 μg/ml appeared to even promote the growth of the non-cancerous cells. These results indicated the nontoxic nature of cobaltocenium-containing polymer PNCCl to non-cancerous cells at least within the concentration range tested in this study. However, PNCCl with a concentration of 100 μg/ml showed significant toxicity to the cancerous PC-3 prostate cells, as demonstrated in another series of images which was further confirmed by the quantitative data of the cell proliferation shown in FIG. 8B. Interestingly, the polymer at a concentration of 25 μg/ml could significantly damage the cancer cells in just 1 hour incubation. However, the cells recovered from the initial (non-lethal) damage and proliferated normally just like the control cancer cells in 72 h (3 days). Therefore, a polymer concentration of ≥100 μg/ml was needed to significantly destroy the cancer cells in the long run. Surprisingly, toxicity of the corresponding monomer NCCl that was used to synthesize polymer PNCCl was almost negligible to both the non-cancerous C3H10T1/2 cells and the cancerous PC-3 cells. The antiproliferative capability of the polymer PNCCl in destroying the cancer cells might be a result of enhanced uptake of the material in the form of macromolecules with multiple repeat units of monomer.

Taken together, toxicity of PNCCl was considered to be negligible to non-cancerous mensenchymal stem cells, but significant to prostate cancer cells, at least within the tested concentration range. These results indicated the potential of water-soluble cobaltocenium-containing polymers as prodrugs for effective cancer treatment with minimal side effects.

Example 4

Use of Cobaltocenium-Containing Polymers as Electrodes

The use of cobaltocenium-containing polymers as electrodes for rechargeable electrochemical batteries was explored via study of the performance of polymer-based electrodes for light-weight flexible secondary batteries. Most of the commercial rechargeable batteries (e.g. Li-ion batteries) are based on metal electrodes, as most metals (metal oxides or metal ions) meet the requirement on reversible electrochemical reactions in both cathode and anode electrodes. However, metal-based electrode materials are heavy, rigid (no flexibility) and are not environmentally benign, not suitable for many portable electronic equipments. Recently, organic polymers particularly conjugated polymers have been introduced for applications in rechargeable batteries. These polymer based batteries are promising because polymers have advantages such as light weight, good mechanical flexibility and environmentally friendly properties. However these polymer-based batteries usually suffer low cycle life and electrochemical instability due to the oxidation and degradation of conjugated polymeric framework.

Figure 9:
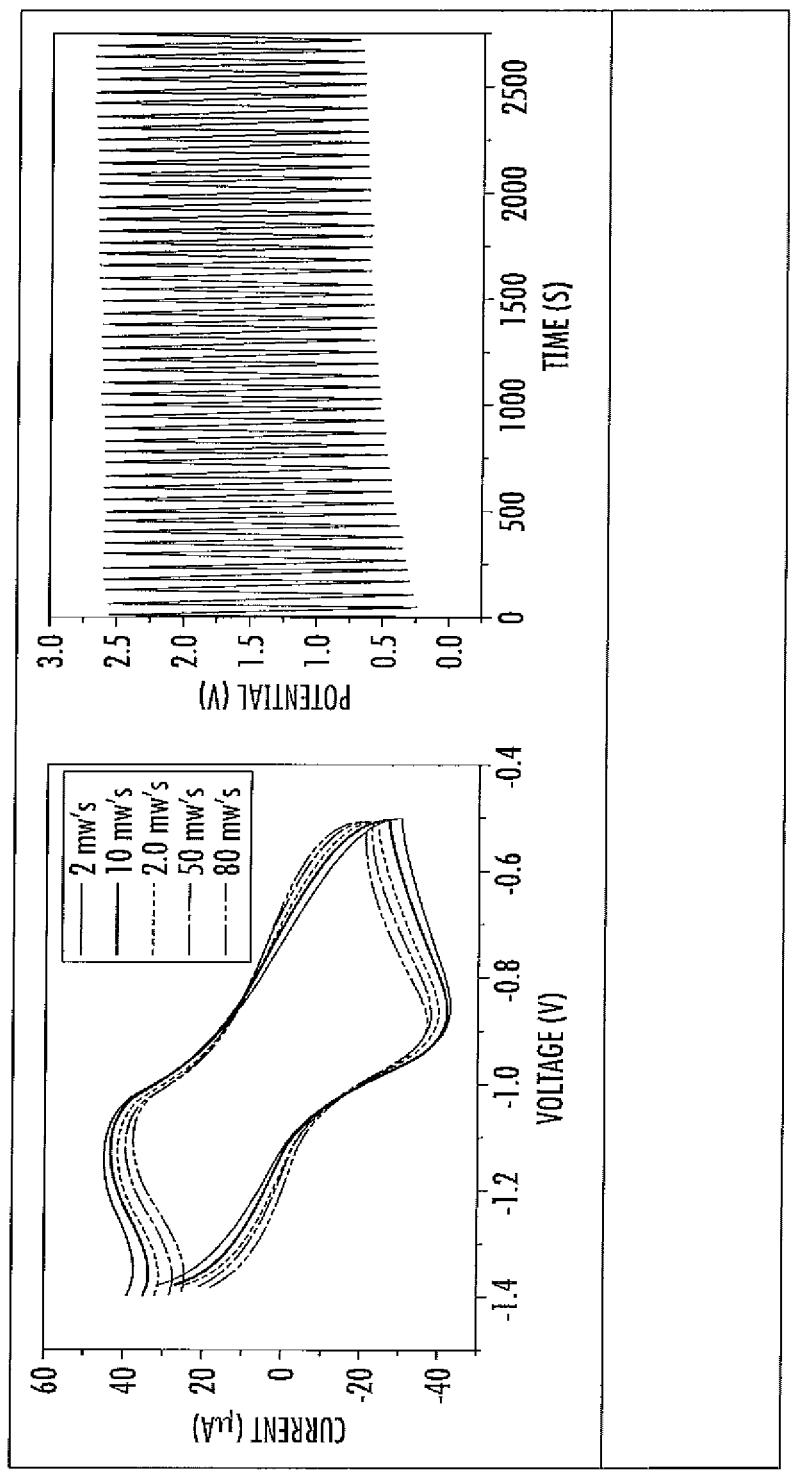
FIG. 9 shows the CV measurements and charging-discharging cycles of cobaltocenium-containing homopolymers, according to the Examples.

It was demonstrated that cobaltocenium-containing polymers have good electrochemical stability, which is expected to provide better cycle life of batteries. The CV of polymers PNCPF6 in DMF showed two similar peaks in one cycle, the peak to peak splittings (ΔEp) of the cathodic and anodic peaks were about 200 mV, and the peak currents of the redox process were equal, indicating a reversible one-electron transfer process (FIG. 9). CV studies of polymers PNCPF6 also showed very little change in peak current with broad range of scanning rate. A simple cell was also set up with cobaltocenium polymers coated on both flat carbon electrodes, with 2 M NaCl aqueous solution as an electrolyte. Before discharging, the electrodes were charged to separate the two electrodes to oxidized state (cobaltocenium) and reduced state (cobaltocene) respectively. The cobaltocenium polymer coated electrodes were stable after cycling for 100 times at a scan rate of 100 mV/s.

Charging and discharging are critical processes in secondary batteries. In the process of both charging and discharging, the anode oxidizes to generate electrons, which are accepted by the cathode to undergo reduction under an external electric circuit. The rechargeable battery can be used repeatedly by charging and discharging cycles and decreases the use of electrolytes and electrodes, which makes them environment friendly. It is essential that charging and discharging processes are reversible and electrode materials are stable to assure longer cycle life and consistent cell stability. In order to increase the voltage gap between two electrodes and avoid potential ion exchange between electrolytes and coated polymers, ferrocene-based polymers can be used, which has a redox potential at 0.55 V vs. SCE, as one of the electrode materials, and aqueous $NaPF_6$ solution as the electrolyte to build a non-organic solvent-based battery. During charging, the anode ferrocene can be oxidized into ferrocenium to generate electrons, while the cathode cobaltocenium can be reduced into cobaltocene, and vice versa for discharging process. Electron transfer takes place only between the electrodes and the redox polymer films via an external circuit.

To increase the charge capacity, polymers can be coated onto a carbon fiber mesh that contains nanoscopic pores, which provides good conductivity and high surface area. To avoid the leakage from using liquid electrolytes, NaPF6 solution can be soaked in a spacer (e.g. filter paper), which can provide a platform to contain the electrolytes. A rechargeable battery can be fabricated with the ferrocene polymer-coated carbon nanofibers and the cobaltocenium polymer-coated carbon nanofibers as two electrodes, while the filter paper-soaked with NaPF6 is sandwiched in between as the electrolyte. Simple encapsulation can be done using aluminum-coated Kapton films to fabricate light-weight flexible secondary batteries.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming a cobaltocenium-containing polymer, the method comprising:
   polymerizing a plurality of cobaltocenium-containing monomers via controlled radical polymerization or controlled ring-opening polymerization, wherein each cobaltocenium-containing monomer comprises a cobaltocenium moiety covalently connected to a polymerizable group.

2. The method as in claim 1, wherein the plurality of cobaltocenium-containing monomers is polymerized via reversible addition-fragmentation chain transfer polymerization.

3. The method as in claim 2, wherein the polymerizable group comprises a vinyl group.

4. The method as in claim 3, wherein the polymerizable group comprises an acrylate moiety, a methacrylate moiety, a styrene moiety, or an acrylamide moiety.

5. The method as in claim 1, wherein the polymerizable group comprises a norbornene moiety.

6. The method as in claim 5, wherein the plurality of cobaltocenium-containing monomers is polymerized via ROMP.

7. The method as in claim 1, wherein the polymerizable group comprises a strained ester ring.

8. The method as in claim 7, wherein the plurality of cobaltocenium-containing monomers is polymerized via ROP.

9. The method as in claim 1, wherein the cobaltocenium-containing polymer is a homopolymer.

10. The method as in claim 1, wherein the cobaltocenium-containing polymer is a copolymer.

11. The method as in claim 10, wherein the copolymer is a block copolymer.

12. The method as in claim 10, wherein the plurality of the cobaltocenium-containing monomer is polymerized with a second plurality of second monomers.

13. The method as in claim 12, wherein the second monomers are non-cobaltocenium-containing monomers.

14. The method as in claim 1, wherein the cobaltocenium moiety is covalently connected to a polymerizable group directly.

15. The method as in claim 1, wherein the cobaltocenium moiety is covalently connected to the polymerizable group indirectly through a linkage between the cobaltocenium moiety and the polymerizable group.

16. The method as in claim 15, wherein the linkage comprises an alkyl group or an alkene group.

17. The method as in claim 15, wherein the linkage comprises an ester group.

18. A cobaltocenium-containing monomer comprising a cobaltocenium moiety covalently connected to a polymerizable group, wherein the polymerizable group is configured to be polymerized via controlled living polymerization or controlled ring-opening polymerization, wherein the polymerizable group comprises a norbornene moiety.

19. The cobaltocenium-containing monomer as in claim 18, wherein the cobaltocenium moiety is covalently connected to the polymerizable group directly.

20. The cobaltocenium-containing monomer as in claim 18, wherein the cobaltocenium moiety is covalently connected to the polymerizable group indirectly through a linkage between the cobaltocenium moiety and the polymerizable group.

21. The cobaltocenium-containing monomer as in claim 20, wherein the linkage comprises an alkyl group or an alkene group.

22. The cobaltocenium-containing monomer as in claim 20, wherein the linkage comprises an ester group.

23. A cobaltocenium-containing polymer formed via polymerization of a plurality of the cobaltocenium-containing monomer as in claim 18.

* * * * *